(12) United States Patent
Hack et al.

(10) Patent No.: US 7,097,859 B2
(45) Date of Patent: Aug. 29, 2006

(54) INDIUM SUPPLEMENT COMPOSITIONS AND METHODS THEREFOR

(76) Inventors: Jacob C. Hack, 826A S. Commerce St., Las Vegas, NV (US) 89106; Richard D. Tobias, 826A S. Commerce St., Las Vegas, NV (US) 89106

( * ) Notice: Subject to any disclaimer, the term of this patent is extended or adjusted under 35 U.S.C. 154(b) by 240 days.

(21) Appl. No.: 10/817,239

(22) Filed: Apr. 5, 2004

(65) Prior Publication Data

US 2005/0220897 A1    Oct. 6, 2005

(51) Int. Cl.
| | |
|---|---|
| *A61K 33/24* | (2006.01) |
| *A61K 31/28* | (2006.01) |
| *A61K 31/522* | (2006.01) |
| *A61K 31/095* | (2006.01) |
| *A61K 31/555* | (2006.01) |
| *A61K 33/00* | (2006.01) |
| *A61K 33/04* | (2006.01) |
| *A61K 33/18* | (2006.01) |
| *A61K 33/30* | (2006.01) |
| *A61K 33/32* | (2006.01) |
| *A61K 33/34* | (2006.01) |
| *A61K 33/42* | (2006.01) |

(52) U.S. Cl. ............... 424/650; 424/602; 424/635; 424/639; 424/643; 424/655; 424/670; 424/688; 424/689; 424/702; 424/724; 424/776; 424/DIG. 6; 514/184; 514/263.31; 514/263.34; 514/492; 514/500; 514/505; 514/560; 514/706; 514/781; 514/960; 514/961

(58) Field of Classification Search ............... 424/602, 424/635, 639, 643, 650, 655, 670, 688, 689, 424/702, 724, 776, DIG. 6; 514/184, 263.31, 514/263.34, 492, 500, 505, 560, 706, 781, 514/960, 961; 426/74
See application file for complete search history.

(56) References Cited

U.S. PATENT DOCUMENTS

| 4,182,754 A | * | 1/1980 | Bonadio | .............. 424/650 |
| 4,359,477 A | * | 11/1982 | Rogers | .............. 514/492 |
| 4,591,506 A | * | 5/1986 | Bonadio | .............. 424/650 |
| 6,007,847 A | * | 12/1999 | Bonadio | .............. 424/650 |

FOREIGN PATENT DOCUMENTS

GB    2384984    *   8/2003

\* cited by examiner

*Primary Examiner*—John Pak
(74) *Attorney, Agent, or Firm*—David Landman

(57) ABSTRACT

A tablet for oral administration of nutritional indium comprises about 10–50 mg indium sulfate, about 4–20 mg caffeine, about 2–10% by weight cocoa powder, and about 5–10% by weight ethyl cellulose, in combination with about 50–150 µg of each of zinc oxide, copper (II) oxide, magnesium oxide, potassium iodide, selenium amino acid chelate, chromium amino acid chelate and manganese amino acid chelate.

8 Claims, No Drawings

INDIUM SUPPLEMENT COMPOSITIONS AND METHODS THEREFOR

FIELD OF THE INVENTION

This invention relates generally to the use of indium as a supplement for human ingestion and more specifically to indium compositions and methods therefor for providing an ingestible supplement for humans in the form of a compressed tablet.

BACKGROUND OF THE INVENTION

Indium is a very soft silver-white metal having an atomic number of 49 and atomic number of about 115. Indium is available in several forms including bar, foil, pieces, powder, nano-sized activated powder, rod, shot, sheet, and wire. The use of indium for industrial applications is widely documented. Indium is generally found in combination with lead compounds. The use of indium as a nutritional supplement is not well known, but purified indium salts that are free of lead salts are known. Such purified indium salts are used in trace quantities as supplements for human consumption for stimulating metabolism.

Several attempts have been made to introduce indium in a digestible form. For example, Bonadio, U.S. Pat. No. 6,007,847 discloses the administration of indium sulfate as a human nutritional supplement. According to Bonadio, U.S. Pat. No. 6,007,847, indium sulfate must be administered either as a solution or as a lozenge which is pre-dissolved in the mouth. Indium sulfate must be taken on an empty stomach and with no other supplement or dietary ingredient mixed with indium sulfate.

Indium sulfate has a bitter, metallic taste which makes it generally unsuitable for administration in the preferred, liquid form disclosed by Bonadio, U.S. Pat. No. 6,007,847. While an indium sulfate tablet would be greatly preferred, Bonadio, U.S. Pat. No. 6,007,847 discloses that because indium sulfate is extremely hygroscopic, it absorbs water and ruins its packaging when formed into pills, capsules and tablets. Bonadio, U.S. Pat. No. 6,007,847 has further disclosed indium sulfate and any GRAS approved indium compounds are poorly absorbed when taken orally.

The applicant of this invention has overcome the above described difficulties by providing a compressed tablet comprising indium salts for oral administration.

SUMMARY OF THE INVENTION

An object of the invention is to provide indium sulfate in a stable, pleasant tasting tablet form.

A further object of the invention is to provide a method for forming indium sulfate tablets which are stable and do not absorb excessive amounts of water.

A yet further object of the invention is to provide substantially non-toxic indium salts in a stable, pleasant tasting tablet form.

A still further object of the invention is to provide a method for forming substantially non-toxic indium salts tablets which are stable and do not absorb excessive amounts of water.

BRIEF DESCRIPTION OF THE PREFERRED EMBODIMENTS

According to one embodiment of the invention a tablet for oral administration of indium comprises, in combination, about 10–50 mg indium sulfate, about 4–20 mg caffeine, about 2–10% by weight cocoa powder, about 5–10% by weight ethyl cellulose, about 50–150 µg zinc oxide, about 50–150 µg copper (II) oxide, about 50–150 µg magnesium oxide, about 50–150 µg potassium iodide, about 50–150 µg selenium amino acid chelate, about 50–150 µg chromium amino acid chelate and about 50–150 µg manganese amino acid chelate.

According to a second embodiment of the invention, a tablet for oral administration of indium consists essentially of:

| | |
|---|---|
| 24 mg (about 7.5% by weight) | indium sulfate, |
| 10 mg (about 3.0% by weight) | caffeine, |
| 100 µg (about 0.03% by weight) | zinc oxide, |
| 100 µg (about 0.03% by weight) | copper II oxide, |
| 100 µg (about 0.03% by weight) | selenium amino acid chelate, |
| 100 µg (about 0.03% by weight) | chromium amino acid chelate, |
| 100 µg (about 0.03% by weight) | manganese amino acid chelate, |
| 100 µg (about 0.03% by weight) | magnesium oxide, |
| 100 µg (about 0.03% by weight) | potassium iodide, |
| 223 mg (about 69% by weight) | dicalcium phosphate, |
| 26 mg (about 8% by weight) | ethyl cellulose, |
| 16 mg (about 5% by weight) | stearic acid, |
| 6.4 mg (about 2% by weight) | silicon dioxide, |
| 1.6 mg (about 0.5% by weight) | magnesium stearate, and |
| 16 mg (about 5% by weight) | cocoa powder. |

According to a third embodiment of the invention, a tablet for oral administration of indium comprises, in combination, at least one indium salt and at least one excipient. The tablet further comprises at least one flavoring, at least one transport agent and at least one trace element component.

According to a fourth embodiment of the invention, a method for producing a tablet for oral administration of indium comprises the steps of providing indium sulfate, caffeine and a portion of cocoa powder in a granulator; providing ethyl cellulose and isopropyl alcohol in a mixer; adding the ethyl cellulose and the isopropyl alcohol to the granulator; granulating a mixture of the indium sulfate, the caffeine, the portion of caffeine, the ethyl cellulose and the isopropyl alcohol; removing substantially all of the isopropyl alcohol by drying the mixture in an oven resulting in a cake; grinding the cake through a mill to provide a granulate; adding dicalcium phosphate and zinc oxide to the granulate; and screening the granulate.

According to a fifth embodiment of the invention, a method for producing a tablet for oral administration of indium comprises the step of providing at least one indium salt and at least one excipient and ingesting the tablet by a person. The method further comprises the steps of providing at least one flavoring for masking the taste of the at least one indium salt; providing at least one transport agent for enhancing the digestion of the at least one indium salt; and providing at least one trace element component for enhancing the utilization of the at least one trace element component in the person.

DETAILED DESCRIPTION OF THE PREFERRED EMBODIMENTS

A tablet for oral administration of indium comprises at least one indium salt and at least one excipient. A tablet may further comprise at least one flavoring. Moreover, a tablet may further comprise at least one transport agent. Additionally, a tablet may further comprise at least one trace element component.

By way of example, each tablet of the invention comprises 10–50 mg of indium sulfate, and preferably 20–30 mg indium sulfate, and most preferably about 24 mg indium sulfate. It is to be understood that other indium salts or combinations of indium salts may also be used in place of indium sulfate provided that indium salts are non-toxic or have a low level of toxicity (for example, a level of toxicity that would qualify for a rating of GRAS ("Generally Regarded As Safe") by the EPA or FDA). Indium salts that may be useful include indium carboxylate (such as acetate, gluconate and palmitate), indium carbonate, indium halides (such as chloride, bromide, iodide and fluoride in various oxidation states), indium nitrate, indium phosphate, indium phosphite, indium sulphate and various indium chelates (one example being ethylenediamine tetraacetic acid) and the like.

Applicant notes that persons who do not do well with indium supplements seem to be lacking reserves of trace elements. Usually, the beneficial effects of indium are enhanced when persons receiving indium also ingest reserves of trace elements such as zinc, copper, selenium and chromium. Therefore, in addition to indium sulfate, a tablet includes other trace element components, preferably in the range of 50–150 μg for each trace element, and most preferably about 100 μg for each trace element. These additional trace element components include zinc oxide, copper (II) oxide, at least one of an amino acid chelate (selenium, chromium and manganese), magnesium oxide and potassium iodide. Each one of the trace element components is present in an amount of about 0.015% to about 0.06% by weight.

The above described ingredients are active ingredients and comprise about 5–10%, preferably about 7.5%, of the weight of each tablet. In addition, about 89–95% and preferably about 89.5%, of the weight of each tablet comprises a combination of at least one flavoring such as cocoa powder, a transport agent such as caffeine and inactive tablet ingredients such as excipients and binders. Examples of excipients and binders are typically dicalcium phosphate, ethyl cellulose, stearic acid, silicon dioxide (usually in the form of micronized silica) and magnesium stearate.

Methylxanthines (such as caffeine, theophylline and theobromine) provide improved transport properties for delivering a suitable dosage of indium salts. It is understood that substantial benefit may still be obtained for a tablet comprising at least an indium salt and at least one excipient without an added transport agent. In at least one embodiment of the invention, equimolar amounts of caffeine and indium salts are suitable components of a tablet. In one embodiment of a formulation including 10–50 mg of indium sulfate, 4–20 mg caffeine provides desirable improved transport properties, and 10 mg of caffeine is preferred.

In at least one embodiment of an indium salts formulation cocoa powder is used as a flavoring. Cocoa powder is added to neutralize the flavor of the indium as the tablet dissolves in the stomach so that no bitterness or metallic taste is evident. Cocoa powder is usually present in an amount of 2–10% by weight, preferably 5%. In yet another embodiment of an indium salts formulation, ethyl cellulose, present in an amount of about 5–10% by weight, is used to delay the release of indium in the stomach.

A preferred tablet according to this invention consists essentially of:

| | |
|---|---|
| indium sulfate | 24 mg (about 7.5% by weight) |
| caffeine | 10 mg (about 3.0% by weight) |
| zinc oxide | 100 μg (about 0.03% by weight) |
| copper II oxide | 100 μg (about 0.03% by weight) |
| selenium amino acid chelate | 100 μg (about 0.03% by weight) |
| chromium amino acid chelate | 100 μg (about 0.03% by weight) |
| manganese amino acid chelate | 100 μg (about 0.03% by weight) |
| magnesium oxide | 100 μg (about 0.03% by weight) |
| potassium iodide | 100 μg (about 0.03% by weight) |
| dicalcium phosphate | 223 mg (about 69% by weight) |
| ethyl cellulose | 26 mg (about 8% by weight) |
| stearic acid | 16 mg (about 5% by weight) |
| silicon dioxide | 6.4 mg (about 2% by weight) |
| magnesium stearate | 1.6 mg (about 0.5% by weight) |
| cocoa powder | 16 mg (about 5% by weight). |

EXAMPLE OF PREPARATION OF TABLETS

In one embodiment of a formulation (described above) a tablet of this invention is made as follows. Indium sulfate, caffeine and a portion of cocoa powder are placed in a granulator. Less than about 16 mg of cocoa powder per about 24 mg of indium sulfate can be used at this stage, although a preferred portion of cocoa powder is about 4 mg per about 24 mg of indium sulfate. In a separate mixer, ethyl cellulose and isopropyl alcohol are mixed for about 20 minutes. The ethyl cellulose and isopropyl alcohol mixture is added to the granulator, and mixed well until granulated, then dried in an oven at about 120° F. (49° C.), substantially removing all of the isopropyl alcohol. The resultant cake is ground through a fitzmill screen size 0093 or the like. The resulting granulate is mixed with dicalcium phosphate and zinc oxide and screened.

Separately, the balance of cocoa powder (preferably about 12 mg per about 24 mg of indium sulfate) is mixed with cellulose, and this mixture (of cocoa powder and cellulose) is screened with magnesium stearate, through a #30 screen, and added to a blender. Copper oxide, amino acid chelates (selenium, chromium and manganese), magnesium oxide, potassium iodide, microcrystalline cellulose, cellulose gum and silica are added to the blender, together with the granulate (indium sulfate, caffeine, ethyl cellulose, dicalcium phosphate and zinc oxide as described above), and blended for about 20 minutes to form a pre-tablet mixture. The pre-tablet mixture is used to form tablets which are stored in an airtight container. The tablets so formed have been found to be stable for extended periods of tire.

The method described is exemplary of one embodiment of an indium sulfate tablet. It is understood that indium sulfate may be replaced with any indium salt or any combination of indium salts as described above. In addition it is understood that variations of transport agents, trace element nutritional supplements, flavorings, excipients and binders may also be used to provide indium salts tablets.

While the disclosure has been particularly shown and described with reference to preferred embodiments thereof, it will be understood by those skilled in the art that the foregoing and other changes in form and details may be made therein without departing from the spirit and scope of the disclosure.

What is claimed is:

1. A tablet for oral administration of indium comprising, in combination: about 10–50 mg indium sulfate, about 4–20 mg caffeine, about 2–10% by weight cocoa powder, about 5–10% by weight ethyl cellulose, about 50–150 μg zinc oxide, about 50–150 μg copper (II) oxide, about 50–150 μg magnesium oxide, about 50–150 μg potassium iodide, about 50–150 μg selenium amino acid chelate, about 50–150 μg chromium amino acid chelate and about 50–150 μg manganese amino acid chelate.

2. The tablet according to claim 1 containing about 20–30 mg indium sulfate.

3. The tablet according to claim 1 containing about 100 μg zinc oxide, about 100 μg copper (II) oxide, about 100 μg magnesium oxide, about 100 μg potassium iodide, about 100 μg selenium amino acid chelate, about 100 μg chromium amino acid chelate and about 100 μg manganese amino acid chelate.

4. The tablet according to claim 1 containing about 5% by weight cocoa powder.

5. A tablet for oral administration of indium consisting essentially of:

| | |
|---|---|
| 24 mg (about 7.5% by weight) | indium sulfate, |
| 10 mg (about 3.0% by weight) | caffeine, |
| 100 μg (about 0.03% by weight) | zinc oxide, |
| 100 μg (about 0.03% by weight) | copper II oxide, |
| 100 μg (about 0.03% by weight) | selenium amino acid chelate, |
| 100 μg (about 0.03% by weight) | chromium amino acid chelate, |
| 100 μg (about 0.03% by weight) | manganese amino acid chelate, |
| 100 μg (about 0.03% by weight) | magnesium oxide, |
| 100 μg (about 0.03% by weight) | potassium iodide, |
| 223 mg (about 69% by weight) | dicalcium phosphate, |
| 26 mg (about 8% by weight) | ethyl cellulose, |
| 16 mg (about 5% by weight) | stearic acid, |
| 6.4 mg (about 2% by weight) | silicon dioxide, |
| 1.6 mg (about 0.5% by weight) | magnesium stearate, and |
| 16 mg (about 5% by weight) | cocoa powder. |

6. A method for producing a tablet for oral administration of indium comprising the steps of:
   providing indium sulfate, caffeine and a portion of cocoa powder in a granulator;
   providing ethyl cellulose and isopropyl alcohol in a mixer and mixing the ethyl cellulose and isopropyl alcohol;
   adding the mixed ethyl cellulose and isopropyl alcohol to said granulator;
   granulating a mixture of said indium sulfate, said caffeine, said portion of cocoa powder, said ethyl cellulose and said isopropyl alcohol;
   removing substantially all of said isopropyl alcohol by drying said mixture in an oven, resulting in a cake;
   grinding said cake through a mill to provide a granulate;
   adding dicalcium phosphate and zinc oxide to said granulate;
   screening said granulate with dicalcium phosphate and zinc oxide to provide a screened mixture of said granulate, dicalcium phosphate and zinc oxide; and
   forming said screened mixture into said tablet; wherein said indium sulfate, caffeine, cocoa powder, ethyl cellulose and zinc oxide are present in sufficient amounts so that said tablet contains about 10–50 mg indium sulfate, about 4–20 mg caffeine, about 2–10% by weight cocoa powder, about 5–10% by weight ethyl cellulose and about 50–150 μg zinc oxide.

7. A method of producing a tablet for oral administration of indium comprising the steps of:
   (1) providing indium sulfate, caffeine and a first portion of cocoa powder in a granulator;
   providing ethyl cellulose and isopropyl alcohol in a mixer and mixing the ethyl cellulose and isopropyl alcohol;
   adding the mixed ethyl cellulose and isopropyl alcohol to said granulator;
   granulating a mixture of said indium sulfate, said caffeine, said first portion of cocoa powder, said ethyl cellulose and said isopropyl alcohol;
   removing substantially all of said isopropyl alcohol by drying said mixture in an oven, resulting in a cake;
   grinding said cake through a mill to provide a granulate;
   adding dicalcium phosphate and zinc oxide to said granulate;
   screening said granulate with dicalcium phosphate and zinc oxide to provide a screened mixture of said granulate, dicalcium phosphate and zinc oxide;
   (2) providing a second portion of cocoa powder;
   mixing said second portion of cocoa powder with cellulose;
   screening said second portion of cocoa powder and said cellulose with magnesium stearate through a screen;
   adding the screened second portion of cocoa powder, said cellulose and said magnesium stearate to a blender;
   adding copper oxide, selenium amino acid chelate, chromium amino acid chelate, manganese amino acid chelate, magnesium oxide, potassium iodide, microcrystalline cellulose, cellulose gum, silica and said screened mixture of step (1) to said blender, forming a pre-tablet mixture;
   blending said pre-tablet mixture; and
   forming the blended pre-tablet mixture into tablets for storage in an air-tight container;
   wherein said indium sulfate, caffeine, first and second portions of cocoa powder, ethyl cellulose and zinc oxide are present in sufficient amounts so that said tablet contains about 10–50 mg indium sulfate, about 4–20 mg caffeine, about 2–10% by weight cocoa powder, about 5–10% by weight ethyl cellulose and about 50–150 μg zinc oxide.

8. The method according to claim 6 wherein said portion of cocoa powder is less than about 16 mg of cocoa powder per about 24 mg of indium sulfate.

* * * * *